(12) United States Patent
Lelievre et al.

(10) Patent No.: US 10,889,780 B2
(45) Date of Patent: Jan. 12, 2021

(54) ORGANIC COMPOUNDS

(71) Applicant: Givaudan SA, Vernier (CH)

(72) Inventors: Dominique Lelievre, Kindhausen (CH); Alain Alchenberger, Zurich (CH); Heinz Koch, Baeretswil (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 16/612,980

(22) PCT Filed: May 14, 2018

(86) PCT No.: PCT/EP2018/062338
§ 371 (c)(1),
(2) Date: Nov. 12, 2019

(87) PCT Pub. No.: WO2018/210725
PCT Pub. Date: Nov. 22, 2018

(65) Prior Publication Data
US 2020/0165539 A1 May 28, 2020

(30) Foreign Application Priority Data
May 15, 2017 (EP) .................... 17171045

(51) Int. Cl.
*A61K 8/18* (2006.01)
*A61Q 13/00* (2006.01)
*A61K 8/00* (2006.01)
*C11B 9/00* (2006.01)

(52) U.S. Cl.
CPC ................ *C11B 9/0034* (2013.01)

(58) Field of Classification Search
CPC ..................................... C11B 9/0034
USPC ............................ 512/24, 22, 8, 1
See application file for complete search history.

(56) References Cited

U.S. PATENT DOCUMENTS 8,383,574 B2 2/2013 Kotachi et al.
2011/0071070 A1 3/2011 Kotachi et al.
2016/0326457 A1* 11/2016 Mishiro ................. A61Q 5/00

FOREIGN PATENT DOCUMENTS

EP 2253695 A1 11/2010

OTHER PUBLICATIONS

Fan et al, Identificatoin of Aroma Compounds in Chinese "moutai" and "Lanjiu" Liquors by Normal Phase Liquid Chromatography Fractionation Followed by Gas Chromatography/Olfactometry, 2012, 311-338 (Year: 2012).*
PCT/EP2018/062338—International Search Report, dated Jul. 2, 2018.
PCT/EP2018/062338—International Written Opinion, dated Jul. 2, 2018.
European Application No. 17171045.2-1468—European Search Report, dated Jul. 17, 2017.
Jutta Reiners, et al., *Odorants of Virgin Olive Oils with Different Flavor Profiles*, J. Agric. Food Chem., Jun. 26, 1998, pp. 2754-2763, vol. 46, American Chemical Society.
Laura Franitza, et al., *Characterization of the Key Aroma Compounds in Two Commercial Rums by Means of the Sensomics Approach*, J. Agric. Food Chem., Dec. 30, 2015, pp. 637-645, vol. 64, American Chemical Society.

* cited by examiner

*Primary Examiner* — Jessica Whiteley
(74) *Attorney, Agent, or Firm* — Curatolo Sidoti Co., LPA; Salvatore A. Sidoti; Floyd Trillis, III

(57) ABSTRACT

Disclosed are fragrance compositions comprising ethyl cyclohexanoate.

12 Claims, No Drawings

ORGANIC COMPOUNDS

CROSS REFERENCE TO RELATED APPLICATIONS

This application is a national stage application of International Application No. PCT/EP2018/062338, filed 14 May 2018, which claims priority from European Patent Application No. EP 17171045.2, filed 15 May 2017, which applications are incorporated herein by reference.

This disclosure relates to fragrance compositions and to a method of enhancing them.

Fragrance compositions are usually blends of volatile individual ingredients, both natural and synthetic, carefully blended by skilled perfumers to bring out an overall desired hedonic character. The individual ingredients are selected to add to this particular desired character.

A very common class of fragrance ingredient is the ester. Esters are found in the essential oils of many plants and are known for their sweet, fruity odor. As a result, they are a popular choice for fragrance compositions. Typical examples of popular fragrance esters include benzyl acetate, bornyl acetate (1,7,7-trimethylbicyclo[2.2.1]heptan-2-yl acetate), 2-tert-butyl-cyclohexylacetate (Agrumex™) and octahydro-4,7-methano-3aH-indene-3a-carboxylic acid, ethyl ester (Fruitate™), and 1,3-cyclohexadiene-1-carboxylic acid, 2,6,6-trimethyl-, ethyl ester (Ethyl Safranate™). All of these are known to have pleasant, desirable odors.

It has now been found that the addition of a particular ingredient can enhance the desirable characteristics of ester-containing fragrance compositions. There is therefore provided a fragrance composition comprising a blend of fragrance ingredients, at least one of which ingredients is an ester, the composition additionally comprising up to 1% by weight of ethyl cyclohexanoate.

Ethyl cyclohexanoate, sometimes referred to as ethyl cyclohexyl carboxylate (CAS 3289-28-9), has an odour described as "fruity, cheesy, winey" In the database of the Good Scents Company, a well-known flavour and fragrance resource. It is known to occur in various natural oils, for example, in virgin olive oil (see, for example, Reiners et al, J. Agric. Food Chem. 1998, 46, 2754-2763) and rum (see Franitza et al, J. Agric. Food Chem. 2016, 64, 637-645). However, although known and characterized, it has never been produced as a commercial fragrance material and there is no disclosure of fragrance compositions comprising said compound.

It has been found uniquely to enhance the odour characteristics of esters; it has no perceptibly effect on other class of fragrance ingredients, such as alcohols, ketones or aldehydes.

Moreover, it has been found that, in order to achieve this desirable effect, the proportion of ethyl cyclohexanoate must be used within strict limits—too little, and there will be no enhancing effect, too much and there will be an undesirable "cheesy" odor. The ethyl cyclohexanoate should therefore be used at concentrations up to 1% by weight, preferably from 0.000001 to 0.05% by weight, e.g., between 0.00001-0.1% by weight, which includes 0.0001-0.02% by weight (e.g., 0.0005% or 0.001%), based on the fragrance composition. However the amounts of ethyl cyclohexanoate present in a fragrance composition may vary, depending on the other fragrance ingredients present. In a further aspect of the present invention, the ratio of ethyl cyclohexanoate to ester should preferably be used within strict limits to avoid that the undesirable "cheesy" odor will be recognized. The ethyl cyclohexanoate should therefore be used at a weight ratio of from 1:10'000'000 to 1:100 (such as 1:5'000'000 to 1:500, which includes 1:1'000'000 to 1:1'000) of the ester component of the fragrance composition (ethyl cyclohexanoate:ester(s)).

There is also provided a method of enhancing the fragrance quality of a fragrance composition containing at least one ester, comprising the addition thereto of up to 1% by weight (e.g. 0.000001, 0.00001, 0.00005, 0.0001, 0.0005, 0.001, 0.01, 0.02, 0.05, 0.1, 0.2, 0.5% by weight) of ethyl cyclohexanoate.

In a further embodiment there is provided a method of enhancing the odor characteristics of esters, in particular of esters providing fruity odor characteristics. By "enhancing the fruity character" is meant that the addition of ethyl cyclohaxane-carboxylated results odor characteristics which are preserved as more juiciness and more natural overall character. Thus there is provided a method of enhancing the fruity characteristics of esters, in particular esters of formula (I) as herein below defined, comprising the step of adding ethyl cyclohexanecarboxylate to a flavor or fragrance composition. For example it enhances the impression of juiciness and ripe fruits such as grapefruit, mango, citrus, orange and the like.

By "enhancing" is meant that the hedonic qualities of the ester, and of the fragrance composition in which it is incorporated, are improved from the point of view of being not only more pleasant, but also more balanced, more natural and/or more intense. The overall hedonic effect is much improved and more desirable, and in general more preferred compared to compositions which are free of ethyl cyclohexanoate.

By "ester" is meant a hydrocarbon compound comprising at least one ester group (—C(O)O—). Lactones, such as γ-decalactone (6-pentyltetrahydro-2H-pyran-2-one); γ-undecalactone (5-heptyloxolan-2-one), which are cyclic esters are also included. Optionally, the hydrocarbon compound may comprise other (e.g., one, two or three) functional group(s), such as, alcohol (—OH), carbonyl (—C(O)—), and ether (—O—). The ester having a molecular weight of up to 300 MW, preferably between 130 and 250 MW.

In a preferred embodiment the ester is a compound of formula (I)

(I)

having a molecular weight of up to 300 (e.g. 130 to 250) and wherein i) $R^1$ is selected from methyl, ethyl, $C_3$ to $C_6$ alkyl, and $C_2$ to $C_6$ alkenyl (for example, hexenyl, prop-2-enyl), and
  $R^2$ is a hydrocarbon radical containing up to 14 C-atoms (for example 5, 6, 7, 8, 9, 10 or 11 C-atoms), optionally comprising one, two, or three functional groups selected from —OH (alcohol), —C(O)-(carbonyl), and ether (—O—); or ii) $R^1$ is a hydrocarbon radical containing up to 14 C-atoms (for example 5, 6, 7, 8, 9, 10 or 11 C-atoms), optionally comprising one, two, or three functional groups selected from —OH (alcohol), —C(O)-(carbonyl), and ether (—O—), and
  $R^2$ is selected from methyl, ethyl, $C_3$ to $C_6$ alkyl, or $C_2$ to $C_6$ alkenyl (for example, hexenyl, prop-2-enyl); or iii) $R^1$ and $R^2$ forming together with the atoms to which they are attached a cyclic ester containing 5 or 6 ring atoms, wherein the ring is optionally substituted with one, two or more groups selected from alkyl and alkenyl.

As used in relation to compounds of formula (I) unless otherwise indicated "hydrocarbon radical" includes linear, branched, mono-, bi- or tri-cyclic alkyl, linear, branched, mono-, bi- or tricyclic alkenyl (comprising one or more double bonds), and aryl, wherein the ring (such as cyclic alkyl, cyclic alkenyl, aryl) is optionally substituted with alkyl.

Non-limiting examples of esters are compounds of formula (I) wherein either $R^1$ or $R^2$ is not alkyl.

Further, non-limiting examples of esters are compounds of formula (I) wherein the hydrocarbon radical comprises 5 to 10 C-atoms.

Further, non-limiting examples of esters are compounds of formula (I) wherein $R^1$ and $R^2$ forming together with the atoms to which they are attached a cyclic ester containing 5 or 6 ring atoms, wherein the ring is substituted with one linear $C_1$-$C_{12}$ alkyl (e.g., $C_3$, $C_4$, $C_5$, $C_6$, $C_7$, $C_8$, $C_9$ alkyl), or one linear $C_3$-$C_{10}$ alkenyl (comprising on or more double bonds, e.g., $C_4$, $C_5$, $C_6$ alkenyl).

Further, non-limiting examples of esters are compounds of formula (I) wherein $R^1$ and $R^2$ forming together with the atoms to which they are attached a cyclic ester containing 5 or 6 ring atoms, wherein the ring is substituted with methyl and one linear $C_1$-$C_{12}$ alkyl (e.g., $C_3$, $C_4$, $C_5$, $C_6$, $C_7$, $C_8$, $C_9$ alkyl), or with methyl and one linear $C_3$-$C_{10}$ alkenyl (comprising on or more double bonds, e.g., $C_4$, $C_5$, $C_6$ alkenyl).

Further specific examples of known esters according to formula (I) are: cedryl acetate ((1 S,6R,8aR)-1,4,4,6-tetramethyloctahydro-1H-5,8a-methanoazulen-6-yl acetate); Helvetolide® (2-(1-(3,3-dimethylcyclohexyl)ethoxy)-2-methylpropyl propionate); 4,8-dimethyl-2-(propan-2-ylidene)-1,2,3,3a,4,5,6,8a-octahydroazulen-6-yl acetate; 4-(tert-butyl)cyclohexyl acetate; ethyl 2-methylpentanoate (Manzanate); hexyl salicylate; methyl 3-oxo-2-pentylcyclopentaneacetate (Hedione); 2-tert-butyl-cyclohexylacetate (Agrumex™); octahydro-4,7-methano-3aH-indene-3a-carboxylic acid, ethyl ester (Fruitate™); and 1,3-cyclohexadiene-1-carboxylic acid, 2,6,6-trimethyl-, ethyl ester (Ethyl Safranate™). Further specific esters according to formula (I) are methyl 2,4-dihydroxy-3,6-dimethylbenzoate (CAS 4707-47-5); allyl heptanoate (CAS 142-19-8); dimethyl benzyl carbinyl acetate (CAS 151-05-3); dimethyl benzyl carbinyl butyrate (CAS 10094-34-5); ethyl 2-methylbutanoate (CAS 7452-79-1); 3a,4,5,6,7,7a-hexahydro-1H-4,7-methanoinden-6-yl propionate (CAS 68912-13-0); and (Z)-hex-3-en-1-yl acetate (CAS 3681-71-8).

The esters may be synthetic ingredients or they may occur in natural fragrance oils. The individual esters present in a known natural fragrance oil can be found by reference to Journals commonly used by those skilled in the art such as "Perfume and Flavourist" or "Journal of Essential Oil Research", or listed in reference texts such as the book by S. Arctander, Perfume and Flavor Chemicals, 1969, Montclair, N.J., USA and more recently re-published by Allured Publishing Corporation Illinois (1994).

A fragrance composition as hereinabove described may, in addition to at least one ester, contain any of the other natural or synthetic ingredients known to the art to be useful in fragrance compositions. Non-limiting examples of such compositions include essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-tnmethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo [4.1.0]heptane-2,5'-[1,3]dioxane]);

macrocycles, e.g. Ambrettolide ((2)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

Fragrance composition comprising ethyl cyclohexanoate and at least one ester, as hereinabove described, may be used in a broad range of fragranced articles, for example, in any field of fine and functional perfumery, such as perfumes, air care products, household products, laundry products, body care products and cosmetics.

The composition can be employed in widely varying amounts, depending upon the specific application and on the nature and quantity of other odorant ingredients. The proportion is typically from 0.1 to 20 weight percent of the application. In one embodiment, the composition of the present invention may be employed in a fabric softener or shampoo in an amount of from 0.2 to 1.5 weight percent (e.g. 0.8-1 weight %). In another embodiment, the fragrance composition comprising ethyl cyclohexanoate and at least one ester may be used in fine perfumery in amounts of from 5 to 20 weight percent (e.g. up to about 30 weight percent). However, these values are given only by way of example, as the experienced perfumer may also achieve effects or may create novel accords with lower or higher concentrations.

Moreover it has been found, that the odor performance is enhanced when a fragranced article comprising a fragrance composition as hereinabove described, is diluted with water. Thus, there is provided as one specific embodiment, the use of a fragrance composition comprising ethyl cyclohexanoate and at least one ester, as hereinabove described, in rinse-off products, such as shampoo, and shower gel, but also in high dilutions in water, like hand wash fabric detergents (liquid or powder) or multi-purpose floor cleaners.

It was also observed that ethyl cyclohexanecarboxylate significantly reduces a perceived malodor, such as kitchen malodor, bathroom malodor, sweet malodor and the like. Thus one may cited as a further example air care products to which ethyl cyclohexanecarboxylate may by admixed.

The fragrance composition as described hereinabove may be employed in a consumer product base simply by directly mixing the fragrance composition with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof.

All percentages and ratios as used herein are by weight unless otherwise indicated.

The invention is now further described with reference to the following non-limiting examples. These examples are for the purpose of illustration only and it is understood that variations and modifications can be made by one skilled in the art.

EXAMPLE 1: SYNTHESIS OF ETHYL CYCLOHEXANOATE

Cyclohexanecarboxylic acid (64 g, 0.50 mol) and p-toluenesulfonic acid (1.0 g, 0.01 mol) in cyclohexane (64 g) were heated to 73° C. Ethanol (64 g, 1.39 mol) was added over 90 min and the reaction mixture was stirred at reflux for an additional 90 min while the aq. phase was gradually eliminated over time. After cooling the reaction mixture to r.t., the org. phase was washed with $H_2O$, 4% aq. $Na_2CO_3$-solution and $H_2O$. The org. phase was concentrated and distilled to yield 73 g (93%) of ethyl cyclohexanecarboxylate as a colorless oil.

$^1$H NMR ($CDCl_3$, 400 MHz): δ=4.09 (q, J=7.1 Hz, 2H), 2.25 (tt, J=11.3, 3.7 Hz, 1H), 1.90-1.83 (m, 2H), 1.78-1.70 (m, 2H), 1.64-1.58 (m, 1H), 1.46-1.36 (m, 2H), 1.31-1.17 (m, 3H), 1.22 (t, J=7.1 Hz, 3H) ppm.

$^{13}$C-NMR ($CDCl_3$, 100 MHz): δ=176.0 (s), 59.9 (t), 43.2 (d), 29.0 (2t), 25.7 (t), 25.4 (2t), 14.2 (q) ppm.

MS (EI, tR=4.89 min): 156 (43, [M]$^+$), 128 (21), 115 (16), 111 (41), 110 (23), 101 (68), 88 (21), 83 (100), 82 (17), 81 (17), 73 (21), 68 (15), 67 (16), 55 (79), 54 (11), 41 (38), 39 (20), 29 (30), 27 (20).

EXAMPLE 2

The following solutions were prepared.
A) 0.1 weight % of ethyl cyclohexanoate in ethanol
B) 10 weight % of fragrant ingredient in ethanol
The two alcoholic solutions above were mixt at a ratio of 1:1.

Both, solution B alone and the mixture of A+B was olfactively evaluated in a triangular test on a blotter in a randomized order. The trained panel was asked to describe the olfactory difference, if any. The results are summarized in Table 1 below.

TABLE 1

| | | B - compound | odor description of the mixture |
|---|---|---|---|
| Ester | I-1 | benzyl acetate (CAS 140-11-4) | ± |
| | I-2 | bornyl acetate (CAS 125-12-2) | ± (more depth, more agrestic, more juicy fir needle) |
| | I-3 | linalyl acetate (CAS 115-95-7) | ± (bergamot candy) |
| | I-4 | 4-(tert-butyl)cyclohexyl acetate (CAS 32210-23-4) | ± |
| | I-5 | Argumex (CAS 88-41-5) | ± (more juicy, natural fruity apple, less chemical fresh) |
| | I-6 | Fruitate (CAS 80623-07-0) | ± (natural, increases lift & juiciness |
| | I-7 | Hedione (CAS 24851-98-7) | ± |
| | I-8 | Manzanate (CAS 39255-32-8) | ± (more natural, juicy, overripe apple flesh) |
| | I-9 | Hexyle salicylate (CAS 6259-76-3) | ± (fresh, minty winter green leaf association) |
| | I-10 | Ethyl Safranate (CAS 35044-59-8) | ± (more lift, more fruity juicy aromatic, more pleasant) |
| Ketone/ Aldehyde | II-1 | 2,6,10-trimethylundec-9-enal (CAS 141-13-9) | −/− |
| | II-2 | Delta Damascone (CAS 57378-68-4) | −/− |
| | II-3 | 3-(3-isopropylphenyl)butanal (CAS 125109-85-5) | −/− |
| | II-4 | 3-methyl-4-(2,6,6-trimethylcyclohex-2-en-1-yl)but-3-en-2-one (CAS 1335-46-2) | −/− |
| | II-5 | Melonal 2,6-dimethylhept-5-enal (CAS 106-72-9) | −/− |

TABLE 1-continued

| | | B - compound | odor description of the mixture |
|---|---|---|---|
| | II-6 | 4-(4-methoxyphenyl)butan-2-one (CAS 104-20-1) | –/– |
| | II-7 | 3-(4-isobutyl-2-methylphenyl)propanal (CAS 1637294-12-2) | –/– |
| Alcohol | II-8 | (1-methyl-2-((1,2,2-trimethylbicyclo[3.1.0]hexan-3-yl)methyl)cyclopropyl)methanol (CAS 198404-98-7) | –/– |
| | II-9 | (1-methyl-2-(5-methylhex-4-en-2-yl)cyclopropyl)methanol (CAS 1655500-83-6) | –/– |

±: in the mixture, overall performance of the ester (B) is clearly enhanced, and its character was slightly modified (details given in brackets).
–/–: both ingredients are recognised as individuals, do not combine as such and tend to be less pleasant than the fragrant ingredient (B) alone.

As can be seen from the results above, the addition of ethyl cyclohexanoate to a fragrant ester results in a more pleasant, more balanced, more natural and/or more intense composition which is more preferred compared to the esters alone. On the other hand, such a benefit was not observed when ethyl cyclohexanoate was added to a fragrant aldehyde, ketone or alcohol.

EXAMPLE 3

Ethyl cyclohexanoate (A) was evaluated on blotter in combination with several odorant esters as indicated at different concentrations. The results are shown in Table 2 below.

TABLE 2

| | B | | |
|---|---|---|---|
| A [%] | Ethyl Safranate @10% Ethanol | Fruitate @10% Ethanol | Argumex @10% Ethanol |
| 1 | – – | – – | – – |
| 0.5 | – – | – – | – – |
| 0.2 | – | – | – |
| 0.1 | ± | ± | ± |
| 0.01 | ++ | ++ | ++ |
| 0.001 | ++ | ++ | ++ |
| 0.0001 | + | ++ | ++ |

– –: unpleasant, cheesy animalic
–: becomes cheesy animalic,
±: in the mixture, overall performance of the ester (B) is clearly enhanced, and its character was slightly modified
+: overall character and performance of the ester (B) is mildly enhanced
++: overall character and performance of the ester (B) is clearly enhanced, and the mixture was preferred to (B) alone.

EXAMPLE 4: FRAGRANCE ACCORD SUITABLE FOR SHAMPOO

| Compound/Ingredient | parts by weight 1/1000 |
|---|---|
| Agrumex | 40 |
| Allyl Heptanoate | 25 |
| Benzyl Acetate | 20 |
| Citronellol | 20 |
| Cyclohexal | 24 |
| Delta Damascone | 1 |
| Dihydro Myrcenol | 50 |
| Dimethyl benzyl carbinyl acetate | 15 |
| Dimethyl benzyl carbinyl butyrate | 5 |
| Dipropylene Glycol (DPG) | 177 |
| Ethyl 2-Methylbutanoate | 7 |
| Evernyl (methyl 2,4-dihydroxy-3,6-dimethylbenzoate) | 8 |
| Fixolide (1-(3,5,5,6,6,8,8-hexamethyl-5,6,7,8-tetrahydro naphthalen-2-yl)ethan-1-one) | 30 |
| Florocyclene (3a,4,5,6,7,7a-hexahydro-1H-4,7-methanoinden-6-yl propionate) | 20 |
| Galaxolide (4,6,6,7,8,8-hexamethyl-1,3,4,6,7,8-hexahydro-cyclopenta[g]isochromene) | 120 |
| cis-3-Hexen-1-ol | 3 |
| (Z)-Hex-3-en-1-yl acetate | 3 |
| 2-Benzylideneoctanal | 50 |
| Beta Ionone ((E)-4-(2,6,6-trimethylcyclohex-1-en-1-yl)but-3-en-2-one) | 60 |
| Iso E Super | 20 |
| Lilial (3-(4-(tert-butyl)phenyl)-2-methylpropanal) | 50 |
| Linalool | 30 |
| Manzanate | 3 |
| Orange oil | 60 |
| Peach Pure (γ-undecalactone) | 10 |
| 2-phenoxyethyl isobutyrate | 140 |
| Tricyclal (2,4-dimethylcyclohex-3-ene-1-carbaldehyde) | 6 |
| Ethyl cyclohexanoate (at a dilution as indicated in Table 3 below) | 3 |
| Total: | 1000 |

The fragrance accord comprising 29.6 weight % of esters according to formula (I) and a variable amount of ethyl cyclohexanoate (A) in DPG as indicated in Table 3, first column, was assessed by a trained panel neat (on a blotter), in a shampoo (fragrance accord @ 0.5 weight %), and in a shampoo (fragrance accord @ 0.5 weight %) diluted with water. The results are given in Table 3 below.

TABLE 3

| | (A) [%] | on blotter | in shampoo | 2 ml shampoo in 50 ml water |
|---|---|---|---|---|
| 4.1 | 10.0 | Over ripe unpleasant | Over ripe, sweaty animalic, unpleasant | Over ripe, sweaty animalic, unpleasant, more lift, more intense, but unpleasant |
| 4.2 | 1.0 | more juicy more green more intense | intense juicy fruity apple, starts to cover over all perfume character, still liked | intense juicy fruity apple, starts to cover over all perfume character, still liked |
| 4.3 | 0.1 | push green pineapple esters, more aggressive | already benefit, more natural, more juicy, more pleasant, more depth, more intensity, clear benefit, preferred to 4.2 | already benefit, more natural, more juicy, more pleasant, more depth, more intense, clear benefit, preferred to 4.2 |
| 4.4 | 0.01 | dear and good benefit, push juicy | already benefit, more natural, more juicy, more pleasant, more depth, more intense, clear benefit, more lift, more freshness, effect even more noticeable | already benefit, more natural, more juicy, more pleasant, more depth, more intense, clear benefit, more lift more freshness, effect even more noticeable, liked, preferred to 4.3 |
| 4.5 | 0.001 | more juicy already benefit | already benefit more natural more juicy more pleasant | already benefit, more natural, more juicy, more pleasant, rounder, less green aggressive, more consumer appeal, more natural |

As can be seen from the summary of the olfactory description of the fragrance accord in Table 3 above, the positive effect of ethyl cyclohexanoate on esters is more effective than the findings with regard to alcohols, aldehydes and ketones taken alone, resulting in an hedonically more pleasant fragrance formulation.

The invention claimed is:

1. A fragrance composition comprising ethyl cyclohexanecarboxylate and at least one odorant ester, wherein the weight ratio between the ethyl cyclohexanecarboxylate and the at least one odorant ester is from 1:10,000,000 to 1:100 (ethyl cyclohexanecarboxylate:ester).

2. The fragrance composition according to claim 1 wherein the odorant ester is a compound of formula (I)

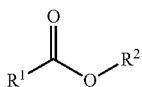

(I)

having a molecular weight of up to 300 and wherein
i) $R^1$ is selected from methyl, ethyl, $C_3$ to $C_6$ alkyl, and $C_2$ to $C_6$ alkenyl, and
   $R^2$ is a hydrocarbon radical containing up to 14 C-atoms, optionally comprising one, two, or three functional groups selected from —OH, —C(O), and —O—; or
ii) $R^1$ is a hydrocarbon radical containing up to 14 C-atoms, optionally comprising one, two, or three functional groups selected from —OH, —C(O), and —O—, and
   $R^2$ is selected from methyl, ethyl, $C_3$ to $C_6$ alkyl, and $C_2$ to $C_6$ alkenyl; or
iii) $R^1$ and $R^2$ forming together with the atoms to which they are attached a cyclic ester containing 5 or 6 ring atoms, wherein the ring is optionally substituted with one, two or more groups selected from alkyl and alkenyl.

3. The fragrance composition according to claim 1 wherein the composition comprises up to 1 weight % of ethyl cyclohexanecarboxylate.

4. The fragrance composition according to claim 2 comprising at least one ester of formula (I) as defined in claim 2 with an "enhanced" odor profile obtained by admixing thereto ethyl cyclohexanecarboxylate.

5. The fragrance composition according to claim 4 obtained by admixing up to 1 weight % of ethyl cyclohexanecarboxylate.

6. A fragranced article comprising a fragrance composition as defined in claim 1.

7. A method of enhancing the fruity characteristics of esters, comprising the step of adding ethyl cyclohexanecarboxylate to a composition comprising at least one odorant ester, wherein the weight ratio between the ethyl cyclohexanecarboxylate and the at least one odorant ester is from 1:10,000,000 to 1:100 (ethyl cyclohexanecarboxylate:ester).

8. The method according to claim 7 wherein the odorant ester is a compound of formula (I)

(I)

having a molecular weight of up to 300 and wherein
ii) $R^1$ is selected from methyl, ethyl, $C_3$ to $C_6$ alkyl, and $C_2$ to $C_6$ alkenyl, and
   $R^2$ is a hydrocarbon radical containing up to 14 C-atoms, optionally comprising one, two, or three functional groups selected from —OH, —C(O), and —O—; or
ii) $R^1$ is a hydrocarbon radical containing up to 14 C-atoms, optionally comprising one, two, or three functional groups selected from —OH, —C(O), and —O—, and
   $R^2$ is selected from methyl, ethyl, $C_3$ to $C_6$ alkyl, and $C_2$ to $C_6$ alkenyl; or
iii) $R^1$ and $R^2$ forming together with the atoms to which they are attached a cyclic ester containing 5 or 6 ring atoms, wherein the ring is optionally substituted with one, two or more groups selected from alkyl and alkenyl.

9. The method according to claim 7, wherein up to 0.1 weight % of ethyl cyclohexanecarboxylate is added to the composition based on the total amount of the composition.

10. The method according to claim 8, wherein up to 0.1 weight % of ethyl cyclohexanecarboxylate is added to the composition based on the total amount of the composition.

11. The fragrance composition according to claim 2, wherein the composition comprises up to 1 weight % of ethyl cyclohexanecarboxylate.

12. A fragranced article having a fragrance composition comprising ethyl cyclohexanecarboxylate and at least one odorant ester, wherein the fragranced article consists of perfumes, air care products, household products, laundry products, body care products or cosmetics, and wherein the weight ratio between the ethyl cyclohexanecarboxylate and the at least one odorant ester is from 1:10,000,000 to 1:100 (ethyl cyclohexanecarboxylate:ester).

* * * * *

UNITED STATES PATENT AND TRADEMARK OFFICE
CERTIFICATE OF CORRECTION

PATENT NO. : 10,889,780 B2  
APPLICATION NO. : 16/612980  
DATED : January 12, 2021  
INVENTOR(S) : Dominique Lelievre et al.

Page 1 of 1

It is certified that error appears in the above-identified patent and that said Letters Patent is hereby corrected as shown below:

On the Title Page

Item [30], insert --May 15, 2017 (EP) ................... 17171045.2--.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*